United States Patent [19]

Coirre et al.

[11] 3,997,559

[45] Dec. 14, 1976

[54] N-ACETYL-L-HYDROXY-PROLINE ZINC SALT

[75] Inventors: Paul Coirre, Magnard a Paris; Bertrand Coirre, Ville d'Avray; Jean-Claude Denis, Paris; Jerome Rambaud, Paris; Jean Cahn, Paris, all of France

[73] Assignee: Franco Chimie S.a.r.l., Paris, France

[22] Filed: Dec. 24, 1975

[21] Appl. No.: 644,026

Related U.S. Application Data

[60] Division of Ser. No. 414,294, Nov. 9, 1973, Pat. No. 3,932,638, which is a continuation-in-part of Ser. No. 243,397, April 12, 1972, Pat. No. 3,891,765, which is a continuation-in-part of Ser. No. 81,499, Oct. 16, 1970, abandoned, which is a continuation-in-part of Ser. No. 756,410, Aug. 30, 1968, abandoned.

[52] U.S. Cl. .................... 260/326.22; 260/326.2; 260/326.46; 424/245; 424/274

[51] Int. Cl.² ........................................ C07D 207/16

[58] Field of Search ............................ 260/326.22

[56] References Cited

FOREIGN PATENTS OR APPLICATIONS 4,127  1/1967  France .................... 260/326.22

OTHER PUBLICATIONS

Mix et al.; *Chem. Abst.* vol. 53, col. 4259 (1959).
Patchett et al.; *J.A.C.S.* (1957) pp. 185–192.
Houck et al.; *Chem. Abst.* vol. 58, col. 3765(h) (1963).

*Primary Examiner*—Donld G. Daus
*Assistant Examiner*—Mary C. Vaughn
*Attorney, Agent, or Firm*—William J. Stein; Eugene O. Retter; George W. Rauchfuss, Jr.

[57] ABSTRACT

Derivatives of L-hydroxyproline and their use in the treatment of inflammation and wound healing.

1 Claim, No Drawings

N-ACETYL-L-HYDROXY-PROLINE ZINC SALT

CROSS REFERENCES TO RELATED APPLICATIONS

This is a division of application Ser. No. 414,294, filed Nov. 9, 1973, now U.S. Pat. No. 3,932,638, which is a continuation-in-part of copending application U.S. Ser. No. 243,397, filed Apr. 12, 1972, now U.S. Pat. No. 3,891,765 which is a continuation-in-part of application U.S. Ser. No. 81,499, filed Oct. 16, 1970, now abandoned, which in turn is a continuation-in-part of application U.S. Ser. No. 756,410, filed Aug. 30, 1968, now abandoned.

BACKGROUND OF THE INVENTION

Diseases affecting the connective tissues of the body have been the subject of a great deal of investigation for the past two decades. The essential amino acid L-hydroxyproline is an important constituent of proteins, particularly those proteins comprising the connective tissues. The ready availability of this amino acid or of derivatives thereof, which can be biologically converted to L-hydroxyproline, provides the basis for adjunctive therapy in diseases which affect the replacement or regeneration of such connective tissue.

Derivatives of L-hydroxyproline used in accordance with the present invention have been found to be particularly useful in the treatment of diseases affecting the connective tissues where such tissues are abundant, as for example, in the articulations or connective tissues of the joints. More particularly, these derivatives are useful in the treatment of various degenerative diseases of the joints such as osteoarthritis. In comparison to drugs now in use for the treatment of rheumatic or arthritic diseases, all of which are toxic and moderately active, treatment with the L-hydroxyproline derivatives in accordance with the present invention is characterized by a biological mode of action and also by a nearly complete absence of toxicity and side effects.

Additionally, the derivatives described herein are useful in accelerating protein synthesis in the healing of granulating wounds, such as those of surgical origin. At present only a very few drugs are active on cicatrization, those mostly used being placental extracts such as the extract of Centella Asicetica (Madecassol, Laroche Navarron), and acetylamino 6-hexanoic acid (Plastenan, Choay).

SUMMARY OF THE INVENTION

This invention relates to a method of treating inflammation in mammals which comprises the oral administration to said mammal of a therapeutically effective amount of an L-hydroxyproline derivative having the formula

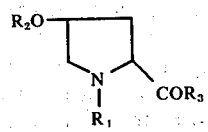

wherein $R_1$ is selected from the group consisting of hydrogen, the hydrochloride salts thereof and the acetyl radical; $R_2$ is hydrogen or the acetyl radical; and $R_3$ is selected from the group consisting of hydroxyl, the non-toxic salts thereof, $NH_2$ and the radical

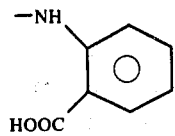

In addition this invention relates to a method of accelerating or promoting the healing of wounds in mammals which comprises the oral administration of said L-hydroxyproline derivatives.

The preferred compounds used in carrying out the methods of this invention are N-acetyl-L-hydroxyproline and its non-toxic salts, the preferred salt being N-acetyl-L-hydroxyproline zinc salt (2:1).

This invention also relates to compounds and pharmaceutical compositions which are useful in carrying out the aforementioned methods of treatment.

DETAILED DESCRIPTION OF THE INVENTION

All of the derivatives described above are simple functional, non-toxic and biologically acceptable derivatives of L-hydroxyproline. Thus, the cyclic α-amino nitrogen may be present in the form of either a free, cyclized secondary amine, as where the symbol $R_1$ is hydrogen, or as a simple acetamide, as for example where the symbol $R_1$ is the acetyl radical. Where these derivatives exist as a free secondary amine ($R_1$ is hydrogen), the hydrochloride salts thereof are also intended to be within the scope of this invention.

The symbol $R_2$ represents either hydrogen or the acetyl radical. When $R_2$ is hydrogen the free alcohol is, of course, present.

The carboxylic acid function is also subject to minor modifications without appreciably altering the biological usefulness of these derivatives. Thus, the simple amides are obtained where the symbol $R_3$ represents the $NH_2$ radical.

The secondary amide obtained by the reaction of 2-amino-benzoic acid or anthranilic acid is defined where the symbol $R_3$ represents the radical

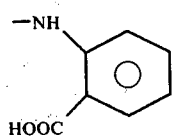

Where $R_3$ represents hydrogen, the parent amino acid is, of course, defined. Also included within the scope of the present invention are the non-toxic carboxylic acid salts. Illustrative of these non-toxic salts are the sodium, potassium, magnesium, calcium, barium, copper, aluminum or silicon salts. Of these non-toxic salts the zinc salt is preferred because of its known astringent properties and its ability to promote wound healing.

Illustrative specific base compounds encompassed by the general formula illustrated above include the compounds N-acetyl-L-hydroxyproline, N,O-diacetyl-L-hydroxyproline, O-acetyl-L-hydroxyproline, α-hydroxyprolinamide, N-acetyl-L-prolinamide and N,O-diacetyl-L-prolinamide or N-acetyl-α-hydroxyprolylanthranilic acid.

MODE OF PREPARATION

The L-hydroxyproline derivatives are prepared by acetylation of the nitrogen of an L-hydroxyproline having the formula,

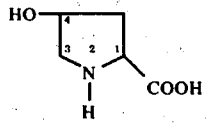

by reaction with acetic anhydride at elevated temperatures, including reflux temperatures, in an acetic acid medium. Additionally or alternatively, acetylation of the oxygen atom in position 4 can be achieved by the reaction with acetyl chloride at a lower temperature in an acetic and hydrochloride acid medium.

L-hydroxyproline or its previously obtained acetylated derivatives are amidified by reaction in the cold, first with ethanol in an anhydrous hydrochloride acid medium, followed by reaction with methanol ammonia.

Salts of the acetylated derivatives of L-hydroxyproline are obtained by reaction of the corresponding acetylated L-hydroxyproline compound in solution with an oxide or hydroxide of the following metals: Na, K, Mg, Ca, Ba, Cu, Zn, Al or Si.

The diacetylated derivatives of L-hydroxyproline are reacted in the cold with methyl anthranilate and the resulting methyl (N,O-diacetyl)-L-hydroxyprolylanthranilate can be hydrolyzed in the cold to yield (N-acetyl) L-hydroxyprolylanthranilic acid.

Detailed procedures are described as follows:

1. Acetylation a. N-acetylation; $R_1 = COCH_3$

Sixteen and seven tenths grams (0.127 mole) of L-hydroxyproline are dissolved in 400 ml. of pure boiling acetic acid. Under rapid boiling and agitation conditions, a mixture of 13.7 ml (0.145 mole) of rectified acetic anhydride and 250 ml of pure acetic acid is added during 25 minutes. Without discontinuing the stirring, the flask content is cooled by simply causing a fresh air circulation externally of the flask until the mixture temperature is reduced to about 35° C. The acetic acid is removed by using a rotary evaporator without exceeding 35° C. under a vacuum of about 15 mm. Hg. After one hour, 30 ml of anhydrous toluene are added, then 10 ml of anhydrous ketone, the mix is homogenized and concentrated again as above for 30 minutes. Then 25 ml of ketone are added again, and subsequently 20 ml of toluene, the product being concentrated again; little by little the solution is converted into an amber colored crystallized paste. Finally, 30 ml of ketone are added to the residue, and stirring is carried out until the oily fraction wrapping the crystals is dissolved. The product is then cooled in an ice chamber, centrifugated and washed with anhydrous ketone, and eventually dried. Yield: 62%; m.p. (Kofler bench): 130° C. After recrystallization in ketone, crystals are obtained, m.p. = 132° C, which constitute the following compound (m.w. = molecular weight and m.p. = melting point):

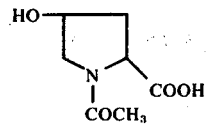

referred to as Co61
N-acetyl L-hydroxyproline
m.w. = 173.17
m.p. = 132° C.

This is a white powder, soluble in water and very soluble in alcohol, insoluble in ether and chloroform, soluble in methanol.

b. O-acetylation; $R_2 = COCH_3$

Two hundred seventy one milligrams (1.56 moles) of N-acetyl L-hydroxyproline are dissolved in 0.5 ml of pure crystallizable acetic acid under magnetic stirring. Subsequently, 0.2 ml of 1.1 N aqueous HCl are added, then, while cooling to 0° C. (ice + water), 2.12 ml (22.4 mole) of pure acetyl chloride are added. The resulting solution is concentrated in vacuo by using a water-jet pump and at 20° C., 2 ml of pure anhydrous toluene are added; the mix is then homogenized and concentrated at a maximum temperature of 25°C. The toluene carry-down operation is repeated by using first, 2 ml and then 1 ml of this solvent, without allowing the temperature to exceed 35° C. The resulting oil is dissolved in 1 ml of pure anhydrous ketone and concentrated at a maximum temperature of 20° C.; the complete mass crystallizes into fine needles a short time thereafter. The last traces of acetic acid are expelled until a constant weight is obtained in a drying apparatus lined with KOH. Yield = 97.5%.

The compound thus obtained has the following composition:

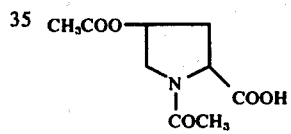

By applying the same method it is possible to use L-hydroxyproline in lieu of N-acetyl hydroxyproline and thus obtain the following compound:

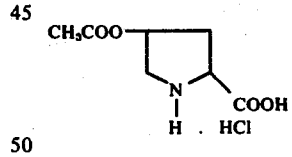

White crystals are obtained which are soluble in water, very moderately soluble in absolute alcohol, insoluble in isopropyl alcohol.

2. Amidification a. From L-hydroxyproline

Fifty grams (0.38 mole) of L-hydroxyproline are weighed and put into 1.5 liters of ethanol. In this suspension, gaseous dry hydrochloric acid is caused to flow through this suspension until the hydroxyproline is dissolved completely, while keeping the temperature at about 10° C. The solution is then evaporated to the dry state, and subsequently carried down once or twice by using ketone. The resulting product is crystallized by using ketone and methanol, and then centrifuged and dried. Thus, 68.3 g (0.35 mole) of crystallized, dry product, having a m.p. = 145° C., are obtained, which consists of hydroxyproline ethylester hydrochloride.

The 68.3 g are dissolved in one liter of a 4N methanol ammonia suspension (4 moles). The mix is allowed to rest at room temperature during 5 to 6 days, then evaporated in the dry state. The product is then crystallized in methanol, centrifuged and dried.

Thus, 46 g (0.276 mole) of L-hydroxyprolinamide hydrochloride are produced as follows:

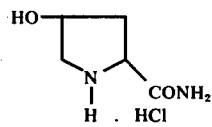
(Referred to as PC 66.1)
m.p. = 215° C.

b. From N-acetyl L-hydroxyproline:

1. In a 3-liter Erlenmeyer flask provided with a pipe dipping to the flat bottom for introducing the gas, and also with a vertical agitator, a thermometer and a gas, and also with a vertical agitator, a thermometer and a calcium chloride tube for venting to the free atmosphere, 1 liter of ethanol and 100 g (0.578 mole) of N-acetyl-4-hydroxy-L-proline are introduced, and gaseous hydrochloric acid is caused to flow through the solution thus obtained and kept at 10° C., until it is saturated.

After allowing to rest during 48 hours, the ethanol is evaporated in vacuo.

The product is centrifuged and filtered.

Thus, 100 g (0.5 mole) of the following ester are obtained:

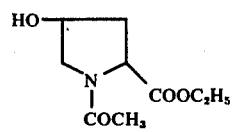
Ethyl N-acetyl-4-hydroxy-L-prolinate
m.p. = 106 to 108° C.

2. One hundred grams (0.5 mole) of ethyl N-acetyl-4-hydroxyl-L-prolinate are mixed with 700 c.c. of 7N methanol ammonia in a thick glass bottle. The bottle is sealed and allowed to rest at room temperature during eight days.

Then the content is filtered and subsequently evaporated in vacuo, the addition of ketone to the residue yielding the crystalline amide.

The acetyl-hydroxyamide is crystallized by using a mixture of 50% methanol and 50% ketone.

After centrifuging and drying, 50 g (0.29 mole) of N-acetyl-L-hydroxyprolinamide are obtained (yield = 58%):

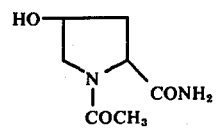
(Referred to as PC 68.5)
N-acetyl L-hydroxyprolinamide
m.p. = 161 to 163° C.

The same procedure is applied starting with (N,O-diacetyl) L-hydroxyproline to obtain (N,O-diacetyl)-L-hydroxyprolinamide.

3. Salts of acetylated derivatives

The acetylated derivatives obtained as per procedure 1 can be converted to the corresponding salts by conventional methods, that is, by reacting the metal oxide or hydroxide with the acetylated derivative in solution form; $Cu(OH)_2$ is used in the case of copper, ZnO in the case of zinc, $Al(OH)_3$ in the case of aluminum, etc.

EXAMPLE:

N-acetyl-L-hydroxyproline, 34.6 gms (0.2 mole) is dissolved in approximately 500 ml of water and heated to effect solution. Finely divided zinc oxide, 8.1 gms (0.1 mole), is slowly added with stirring. Stirring is continued for one hour and the solution permitted to cool. The N-acetyl-L-hydroxyproline zinc salt (2:1) is recovered having the formula:

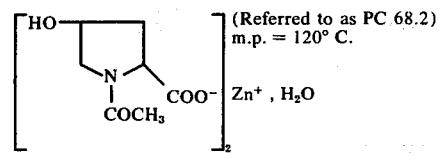
(Referred to as PC 68.2)
m.p. = 120° C.

In addition to zinc, this is applicable to sodium, potassium, calcium, barium, aluminum, silicon, magnesium and copper.

4. Preparation of (N-acetyl) L-hydroxyprolylanthranilic acid

From PC 67.5 [(N,O-diacetyl)-L-hydroxyproline] obtained by carrying out method 1 (b) hereinabove, (N-acetyl) L-hydroxyprolylanthranilic acid, referred to as PC 68.1, can be prepared as follows:

Methyl (N,O-diacetyl) L-hydroxyprolylanthranilate (PC 67.9)

22 156-thousandths grams (0.103 mole) of N,O-diacetyl L-hydroxyproline (PC 67.5), m.p. = 132.5° C., are dissolved in 554 ml of tetrahydrofurane (THF). 31 grams (0.205 mole) of methyl anthranilate are then added, and after the dissolution thereof (during about 30 min.) 42.5 g (0.205 mole) of N,N'-dicyclohexylcarbodiimide are added all at once under magnetic stirring and cooling to 0° C.

After storage during 20 to 24 hours in a refrigerator, with intermittent short manual agitation, the resulting dicyclohexylurea (83% of the theoretical amount, m.p. = 234° C.) is centrifuged, washed with 150 ml of THF, and the filtrate is eventually concentrated in vacuo at 20°–25° C. (max.) until a constant weight is obtained (about 10 hours).

The resulting oil and crystal mixture is heated under reflux conditions with 670 ml of anhydrous petroleum ether (b.p. 40° to 65° C.); the product is allowed to cool to room temperature, decanted, washed with 170 ml of the same solvent, and decanted again.

The same operation is repeated by using 500 ml of petroleum ether for the reflux step and 80 ml for the washing step.

A third treatment conducted with 330 and 40 ml of the same solvent respectively (a centrifugation is substituted however for the decantation) yields, after drying in vacuo, 28 to 29 g (80% of theoretical amount) of raw product (duration of the three treatments = 8 hours):

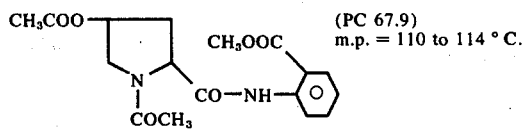
(PC 67.9)
m.p. = 110 to 114 ° C.

After allowing a 19.735-gram (0.0567 mole) suspension of methyl (N,O-diacetyl) L-hydroxyprolylanthranilate (PC 67.9) in a mixture consisting of 518 ml of H₂O and 27.4 ml of NaOH (4.15 N) (0.1134 equivalent) to remain in contact at 0° C. during 70 hours, of which 4 hours is under stirring, the resulting homogeneous solution is passed during 20 min. over 72 ml of ion-exchange resins IR-120 (H⁺) "Amberlite" of the analytic type (height to diameter ratio = 8), the pH value of the eluated substance being about 4.

The resins are washed with 100 ml of H₂O.

The eluate and wash water are concentrated by using 2 to 3 successive jets at 28° C. (max.) in a rotary evaporator in vacuo, followed by centrifugation and drying in vacuo.

Thus, 15.1 g of raw products (91% of the theoretical amount) having a very satisfactory degree of purity are obtained:

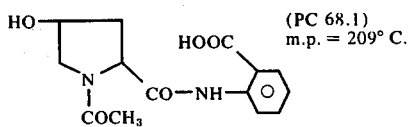

(PC 68.1)
m.p. = 209° C.

The compounds described herein exhibit valuable pharmacological properties. More particularly, these L-hydroxyproline derivatives possess both anti-inflammatory as well as wound healing properties with respect to the connective tissues as determined by the following standard, conventional tests used for evaluating anti-inflammatory activity and cicatrization or wound healing ability.

Turpentine Micro-abcess Test

White male rats weighing about 150–60 grams are used as the test animal. After carefully shaving the skin and disinfecting it with alcohol, the test animals receive a 0.2 ml subcutaneous injection of rectified turpentine oil in the upper-inner portion of the lumbar region. This injection is made following a moderate anesthesia with ether. The animals are then treated 2 hours subsequent to their recovery from the action of the anesthetic drug, treatment being continued during a period of from 5 to 10 days.

The test compounds are all administered by the oral route. Following treatment the animals are sacrificed by decapitation. The granulomas which form are removed, carefully dissected, dried between two sheets of filter paper and weighed. Each granuloma is divided into two fractions, one of which is used for histological examination and the other for a biochemical determination. The left suprarenal gland is removed and examined in order to determine any possible corticotropic effects of the products administered. Each derivative is administered in three doses: 8, 32 and 128 milligrams per kilogram. The results are compared with those obtained from the non-treated or control group as well as those obtained with a group of test animals treated with indomethacine, a known anti-inflammatory agent.

The weight of the granulomas obtained from the groups of animals treated with the test compounds are reduced in comparison to the granulomas obtained from the reference or control group of animals. In addition, these granulomas weighed as much or less than the granulomas obtained from the group of animals which were treated with indomethacine. The water content is unaltered, as well as the rate of desoxyribonucleic acid. The ribonucleic acid rate was incresed significantly. The histochemical study confirmed the results of the biochemical study, namely, the quantity of collagen is significantly reduced in comparison to the control group, and the number of fibroblasts is increased.

The conclusion of the biochemical study is that the compounds involved exert a powerful anti-inflammatory action in mammals which is not necessarily proportional to a system of doses. The term "mammal" refers to warm-blooded higher vertebrates such as mice, rats, guinea pigs, rabbits, ferrets, dogs, cats, horses, cows, and primates, including humans.

Cicatrization

White male rats weighing about 150–160 grams are again used as the test animal. After carefully shaving the skin and disinfecting it with alcohol, the animals are moderately anesthetized with ether. A wound having strictly the same length and depth is made in all of the animals. One group of animals is taken as a control or reference group, while the other animals are treated with the various test compounds. In each group of animals, lots are determined at random for sacrificing the animals as the third, sixth, ninth and twelfth day, the remainder of the animals being sacrificed on the fifteenth day. All of the substances are administered orally at a dose of 8, 32 and 128 milligrams per kilogram. After sacrificing the animals, the wounds are removed in order to study the tensile strength of the cicatrice and for their histological examination.

The following results are obtained. Cicatrization time of the experimental wounds of the test animals treated with the L-hydroxyproline derivatives was about half the time required for similar wound healing in the control group of animals. Examination of the wound sites indicated wound healings which were definitely sharper and which were rapidly being filled by the budding of healthy connective tissue. The cicatrices obtained from the test animals were clean, firm, and both macroscopically and microscopically normal in appearance. Most surprisingly, the hair was beginning to grow again over the cicatrice, a fact not observed in any of the reference animals. Favorable results were obtained with even the smallest dose and were not necessarily proportional to a system of doses for any of the test compounds being examined.

The conclusion is that the L-hydroxyproline derivatives of the present invention exert a trophic action on the connective tissues, which is useful in the cicatrization of accidental or surgical wounds.

The zinc salts of the free carboxylic acid derivative, and particularly the N-acetyl-L-hydroxyproline zinc salt (2:1), are of value in accelerating the healing of granulating wounds. Zinc is known to act as an astringent and cause the shrinkage of edematous tissues. It is also an integral part of a number of enzymes which are important in protein and carbohydrate synthesis in metabolism. Pories et. al., Lancet 1, 121 (1967), have shown that the oral administration of zinc sulfate promotes the healing of granulating wounds caused by surgical excision of pilonidal-sinus tracts. Thus, the combined therapeutic effect of the L-hydroxyproline derivatives on the one hand, and the known therapeutic effect of zinc on the other hand, renders the zinc salts for these compounds of particular value in the present invention.

When an equivalent dosage of zinc sulfate is concomitantly administered with N-acetyl-L-hydroxyproline, patients frequently experience a mild transient gastric discomfort and/or nausea. Attempts to avoid or minimize such occurrences have been made by the administration of the active ingredients with meals. Although reducing the incidence of nausea, the effectiveness of these agents in accelerating wound healing is thereby diminished. Administration of the active ingredients in the form of their N-acetyl-L-hydroxyproline zinc salt (2:1), permits the oral administration of zinc without the concomitant nausea generally associated therewith, and thereby still retain the desired maximum efficacy of the therapeutic agent employed.

When used for their wound healing effects, the compounds of the present invention are administered and used in the same manner and in the same dosage ranges as if they were being used to treat inflammation. The treatment of inflammation in accordance with this invention is accomplished by administering an effective amount of a L-hydroxyproline derivative, particularly the preferred compound N-acetyl-L-hydroxyproline or its non-toxic salts, in a pharmaceutically acceptable carrier. Preferably, the pharmaceutical carrier is in the form of a tablet or capsule.

The non-toxic pharmaceutical carrier may be either solid or liquid. Illustrative of solid carriers are lactose, corn starch, gelatin, talc, stearic acid, magnesium stearate, sucrose, agar, pectin and acacia. Illustrative of liquid carriers are peanut oil, olive oil, sesame oil, saline solution and water. Additionally, the carrier or diluent may include a time delay material such as glyceryl monostearate or glyceryl distearate with or without a wax.

Several pharmaceutical dosage unit forms of the therapeutically useful compositions can be used. For example, if a solid carrier is used, the compositions may take the form of tablets, capsules, powders, troches or lozenges, prepared by standard pharmaceutical techniques. If a liquid carrier is used the preparation may be in the form of a soft gelatin capsule, a syrup or a liquid suspension. Additionally, ointments, pomades or gels can be utilized for topical administration. Parenteral dosage unit forms which are useful for subcutaneous, intramuscular or intravenous administration may also be advantageously employed. To enhance their stability the composition can be frozen after filling into a vial and the water removed under vacuum. The dry lyophilized powder is then sealed in the vial and an accompanying vial of water for injection is supplied to reconstitute the powder immediately prior to use.

The active compounds and compositions of this invention are present in an amount sufficient to treat inflammation. Advantageously, the active ingredients are administered daily in amounts ranging from about 8 to 128 milligrams per kilogram. In humans, the preferred compounds are administered in an amount of from about 4 milligrams to 12 milligrams per kilogram of body weight per day. For an average human weighing 75 kilograms a therapeutically effective amount comprises from about 300 to 900 milligrams of active ingredient administered daily. It should be understood, however, that although preferred dosage ranges are given, the dose level for a given patient depends upon the activity of the specific compound employed. Additionally many other factors which modify the actions of drugs must be taken into account by those skilled in the therapeutic use of medicinal agents, as for example, age, body weight, sex, diet, time of administration, route of administration, rate of excretion, drug combination, reaction sensitivities and severity of the disease.

The compounds of this invention are preferably administered in oral dosage form in dosages which contain from 50 to 200 milligrams per dose. The compounds of choice, and in particular the compounds N-acetyl-L-hydroxyproline zinc salt (2:1), are most preferably administered three to eight times daily in tablet form, each tablet containing 100 milligrams of active substance. Examples of such oral dosage units include the following:

a. N-acetyl-L-hydroxyprolinamide: 100 mg, excipients, q.s. for 1 tablet;

b. N-acetyl-L-hydroxyproline: 100 mg, excipients, q.s. for 1 tablet;

c. N-acetyl-L-hydroxyproline zinc salt (2:1): 100 mg, excipients, q.s. for 1 tablet.

We claim:

1. N-acetyl-L-hydroxyproline zinc salt (2:1).

* * * * *